United States Patent
Blum et al.

(10) Patent No.: US 9,211,208 B2
(45) Date of Patent: Dec. 15, 2015

(54) ORTHOSIS AND PRODUCTION METHOD

(75) Inventors: Thomas Blum, Wiesbaden (DE); Christoph Thiel, Remshalden (DE)

(73) Assignee: WILHELM JULIUS TEUFEL GMBH, Wangen (DE)

( * ) Notice: Subject to any disclaimer, the term of this patent is extended or adjusted under 35 U.S.C. 154(b) by 363 days.

(21) Appl. No.: 13/697,493

(22) PCT Filed: Apr. 20, 2011

(86) PCT No.: PCT/EP2011/056313
§ 371 (c)(1),
(2), (4) Date: Jan. 31, 2013

(87) PCT Pub. No.: WO2011/141283
PCT Pub. Date: Nov. 17, 2011

(65) Prior Publication Data
US 2013/0131569 A1    May 23, 2013

(30) Foreign Application Priority Data

May 11, 2010 (DE) .......... 10 2010 020 259

(51) Int. Cl.
*A61F 5/00* (2006.01)
*A61F 5/01* (2006.01)
(Continued)

(52) U.S. Cl.
CPC ............ *A61F 5/0127* (2013.01); *A61F 5/0111* (2013.01); *B29C 70/36* (2013.01); *B29L 2031/7532* (2013.01)

(58) Field of Classification Search
CPC ........... A61F 2/2487; A61F 2250/0003; A61F 2/2481; A61F 2/0811; A61F 13/067; A61F 5/14; A61F 13/04; A61F 2002/0829; A61F 2002/0835; A61F 2002/0858; A61F 2002/0888; A61F 2/0805; A61F 5/0111; A61F 5/0127; B29C 70/36; B29L 2031/7532

USPC ............. 602/5–8, 16, 20–28, 60–62
See application file for complete search history.

(56) References Cited

U.S. PATENT DOCUMENTS 4,841,958 A * 6/1989 Ersfeld et al. ............ 602/8
4,856,502 A * 8/1989 Ersfeld et al. ............ 602/8
(Continued)

FOREIGN PATENT DOCUMENTS

DE    19604309 A1    8/1997
DE    69732541 T2    2/2006
(Continued)

OTHER PUBLICATIONS

International Search Report for Application No. PCT/EP2011/056313 dated Oct. 12, 2011 (3 pages).

*Primary Examiner* — Michael Brown
(74) *Attorney, Agent, or Firm* — Michael Best & Friedrich LLP

(57) ABSTRACT

An orthosis and a method for the production thereof are provided. The orthosis includes a first support section and at least one further support section that form a three-dimensional support body. The support sections rest on the patient and support limbs or body areas of the patient. The orthosis also comprises fixing means which engage on the support body and which fix the orthosis on the patient. The support body comprising the support sections includes a reinforcing structure that comprises a support layer onto which at least one reinforcing thread is sewn. A pattern layout of the reinforcing thread is oriented along force lines corresponding to stresses that occur in the support body. The layout of the reinforcing thread lies within a surface on the support layer, said surface corresponding to a two-dimensional pattern layout of the three-dimensional support body.

4 Claims, 9 Drawing Sheets

Figures 1, 2:
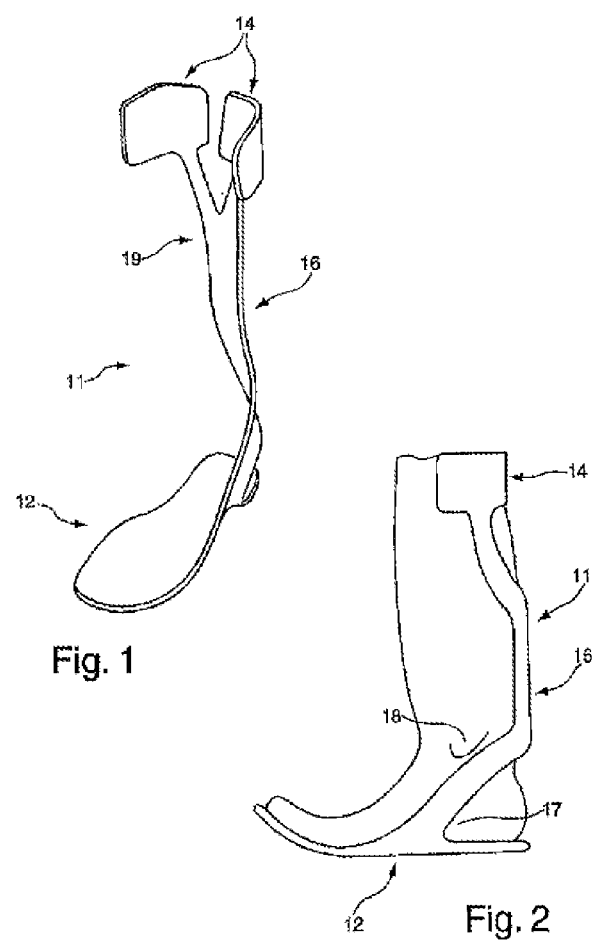

(51) Int. Cl.
  *B29C 70/36*   (2006.01)
  *B29L 31/00*   (2006.01)

(56) References Cited

U.S. PATENT DOCUMENTS

| | | |
|---|---|---|
| 5,826,304 A | 10/1998 | Carlson |
| 6,146,344 A | 11/2000 | Bader |
| 6,171,535 B1 | 1/2001 | Glynn |
| 6,676,618 B2 * | 1/2004 | Andersen ............ 602/7 |
| 7,077,818 B2 * | 7/2006 | Ingimundarson et al. ...... 602/27 |
| 2001/0031935 A1 | 10/2001 | Anderson |

FOREIGN PATENT DOCUMENTS

| | | |
|---|---|---|
| DE | 60315698 T2 | 6/2008 |
| EP | 1379201 B1 | 1/2006 |
| WO | 97/16140 A1 | 5/1997 |

* cited by examiner

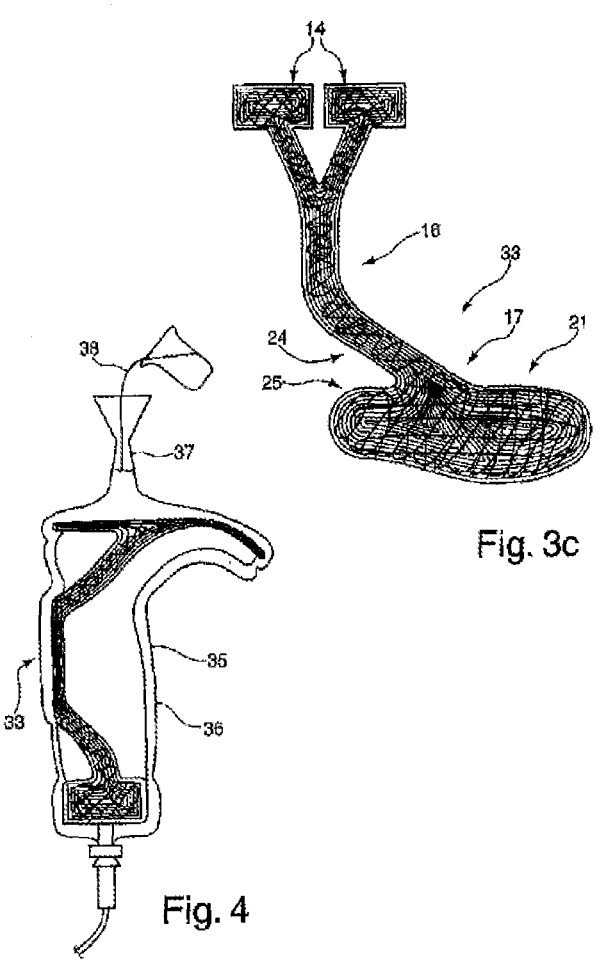

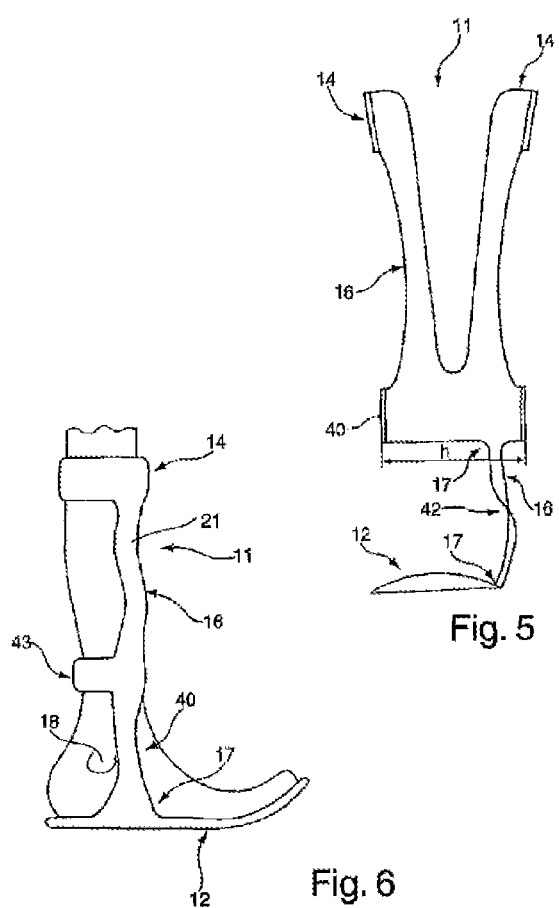

ORTHOSIS AND PRODUCTION METHOD

The invention relates to an orthosis and a method for the production thereof, having a first and at least one other support section, which form at least one spatially formed support body, wherein the support sections are designed to rest on the patient and to support limbs or body areas of the patient.

An orthosis of this type may be designed, for example, as an ankle-foot orthosis. An orthosis of this type is used with people having pronounced foot drop, or by people suffering from a myasthenia in the lower extremities. These orthoses comprise a first support section, which forms, for example, a foot sole or foot plate, as well as on other support section, which engages with the lower leg. A sturdy support body is formed through the connection of the two support sections via a connecting section, which supports the person in walking.

An orthosis of this type is known, for example, from DE 697 32 541 T2. A connecting element is provided between a foot sole as the first support section, and a shinbone attachment as the second support section, which connects the two support sections to one another. A brace is designed, in particular in the transition region between the foot sole and the support section resting on the shinbone, consisting of numerous layers of a carbon fiber textile reinforced with carbon fibers, which is impregnated with an epoxy base material. Numerous layers of carbon fiber textile of different lengths extend from the brace into the foot sole, wherein the carbon fiber textile is designed as strips, and redirected, at least in part, in different directions, in order to extend to the balls and sole of the foot. This configuration ensures, specifically, a durability and stiffness in the transition region between the brace and the foot sole. This has, however, the disadvantage that the wearing comfort is reduced due to the high degree of stiffness. Furthermore, a significant thickening of the brace occurs. This is disadvantageous to the patient, because in the region of the medial and lateral course of the clasp to the foot sole in the shoe, very little space remains, and a strong expansion of the shoe results from the thickening.

A similar design is used, for example, in DE 603 15 698 T2. As a result of the different layering configuration of individual textile layers, a stiffened region is formed, which can accommodate the supporting force, but, however, the wearing comfort is, in turn, significantly reduced.

Another, similar, ankle, or ankle-foot orthosis is known from EP 1 379 201 B1. A lower limb orthotic brace is known from U.S. Pat. No. 6,146,344, in which a tubular multidirectional network consisting of carbon fibers is used. A flexure unit of a joint is known from U.S. Pat. No. 5,826,304, having carbon fibers which provide the unit with a longitudinal strength and stiffness.

The invention assumes the objective of proposing an orthosis and a method for the production thereof, which enables an individual fitting to the load, as well as a high degree of wearing comfort, with a sufficient stiffness and dynamic loading capacity.

This objective shall be attained in accordance with the invention.

The orthosis according to the invention comprises a support body having a first, and at least one other, support section made of at least one reinforcing structure, which comprises a support layer, onto which a continuous bundle of reinforcing fibers are applied, in particular, is sewn or stitched thereto by means of a fastening thread, wherein a layout of the fiber bundle is provided, substantially corresponding to the stresses occurring in the support body, oriented along the lines of stress. The layout of the fiber bundle furthermore occurs substantially within a surface area on the support layer corresponding to a two-dimensional pattern layout of the support body, and said support layer is spatially shaped with the applied fiber bundles, and impregnated with a curable base material, thus forming the support body.

A fiber bundle is understood to be a continuously laid out bundle of reinforcing fibers, which is laid, without breaks, along a given line, which substantially lies within the surface area of the support layer, corresponding to a two-dimensional pattern layout of the support body. Thus, instead of short, separated bundle sections, an "endlessly" long bundle of reinforcing fibers is processed. In doing so, not only is a single fiber bundle substantially laid out within the support body, but instead two or more fiber bundles can also be laid out accordingly. The number of numerous fiber bundles is then, preferably, small, such that a technical effect is obtained corresponding to that of a single fiber bundle. The trimming of the carbon fibers occurring in the production corresponds to how low the number of fiber bundles is. Less trimming results in less formation of carbon dust, and therefore a lower fire hazard.

The given line, along which the fiber bundle is laid out, runs according to the stresses occurring in the support body, substantially oriented along lines of stress. The given line can exhibit substantially straight line sections along the stresses occurring therein, as well as 180° redirections following said straight line sections, such that a back and forth layout of the fiber bundle results following the direction oriented on the lines of stress. The length of the fiber bundle, depending on the orthosis that is to be created, can lie in a preferred range of 20 meters to a few hundred meters, and preferably, with ankle-foot orthoses, in the range of 40-80 meters. Due to the orientation of the fiber bundles oriented along the lines of stress, having reinforcing fibers on the support layer, a support body for an orthosis of this type has the advantage of being able to obtain not only an increased stiffness, but also an increased flexibility, or dynamic load capacity, respectively, with a reduced thickness of the reinforcing structure.

For the formation of the support body, a reinforcing structure is produced in which the fiber bundle is sewn or stitched, in particular, to the support surface within the surface area, corresponding to a two-dimensional layout of the support body. Preferably, the flow of forces of the fiber bundle is not interrupted. A laying out of the fiber bundle, in particular, outside of the surface area, and back into the surface area after redirecting said bundle outside of this surface area, is not desirable, and should not be carried out, or carried out respectively, if applicable, with the exception of the laying out of a supply fiber bundle, which, due to reasons regarding the laying out, is supplied from outside of the surface area. Due to the continuous structure of the bundle of reinforcing fibers, an increased transfer of forces is enabled, by means of which, with a lesser thickness of the reinforcing structure, an equivalent or increased stiffness, in comparison with common orthoses, can already be obtained. A redirection of the laying out direction of the fiber bundle also occurs as a result of the course of the laying out of the fiber bundle within the surface area of the support surface corresponding to the two-dimensional layout of the support body, preferably exclusively within the two-dimensional layout, such that a break in the fiber bundle does not occur.

Preferably, the layout pattern of the, preferably, one bundle having reinforcing fibers, occurs such that the surface area of the support surface, corresponding to a two-dimensional layout of the support body, is substantially, at least for the most part, and preferably entirely, covered by reinforcing fibers. The reinforcing fibers thereby are preferably the fibers of the continuously laid out bundle.

The support layer in this case may be made of a plastic, for example a polyamide textile or polyamide non-woven.

It is, however, also conceivable, that the support layer includes a fiber reinforced non-woven or textile, in particular a carbon fiber or glass fiber reinforced non-woven or textile, or that the support layer is a base layer including reinforcing fibers. In particular, the support layer can also include a crossing pattern of reinforcing fibers, which are similar or identical to the reinforcing fibers of the bundle. With an embodiment of this type, it is then sufficient if the base layer together with the bundle laid out along the stresses occurring in the support body, oriented along lines of stress, substantially covers, at least for the most part, and preferably entirely, the surface area of the support surface corresponding to the two-dimensional layout of the support body.

Preferably, it is provided that the application of the fiber bundle occurs, by means of a fastening thread, through sewing or stitching, or by means of an adhesive, via gluing. Moreover, it is advantageous if the bundle is formed by reinforcing fibers of 3,000-56,000, and preferably 12,000-48,000, and more preferably 24,000-36,000 fibers, in particular carbon fibers, running parallel to one another.

According to a preferred embodiment of the invention, at least one layout layer is provided on the support layer, formed from the continuous, laid out, fiber bundle. This design enables a continuous laying out and, in particular, sewing of the fiber bundle to the support layer, as well as a closed surface, with respect to the flow of forces.

With a further preferred design of the reinforcing structure for production of the support body, it is provided that a bundle of reinforcing fibers are laid out as an edge fiber bundle, in particular, a closed edge fiber bundle, along the edge and/or parallel to the edge of the surface area of the support surface, corresponding to the two-dimensional layout of the support body. This configuration enables, in particular, a reinforcement, or stiffening, respectively, of the reinforcing structure after said structure has been laminated to a curable base material. In this manner, a boundary is obtained, at the same time, for the layout of the fiber bundle, or other fiber bundles, of one or more layout layers on the support layer. In this manner, a connection can also be obtained between an edge fiber bundle of this type, and the sections of the fiber bundle lying therein. The edge region, or the edge fiber bundle, respectively, may have a width in the range of 0.3 cm-3.5 cm, and preferably in the range of 1 cm-2 cm. With a later fitting of the orthosis to the person wearing the orthosis, material may be removed in the edge region, without thereby altering the mechanical properties or durability thereof in a disadvantageous manner.

Another advantageous embodiment of the invention provides that within a layout layer, the fibers of the fiber bundle are disposed in a unidirectional manner and/or such that they run cross-wise to one another. Unidirectional, in this case, means that the fibers are laid out substantially along one direction, back and forth, and substantially parallel to one another and/or parallel to an edge region. This selection for the layout of the fiber bundle is dependent on the respective regions of the orthosis, and their functions, such that the solidity, bending stiffness and torsional strength, as well as the dynamic load capacity of the individual sections can be adjusted accordingly.

Another preferred embodiment of the invention provides that between the at least two support sections, there is at least one connecting section, and the at least two support sections are connected to one another by means of a fiber bundle along the connecting section, which are preferably shaped spatially to one another. As a result, a dynamic load capacity between spatially differently oriented support sections can be determined. At the same time, a simple production is enabled by means of a continuous filament.

Another preferred embodiment of the orthosis provides that the one layout layer extends at least in part in the support section and/or connecting section and/or transition region between the at least one support section and the connecting section. This configuration enables an individually fitted design of the orthosis. By way of example, a support section, such as that running along a foot sole, for example, may have a different stiffness adjusted to the foot sole by this means, in order to fit to a natural rolling motion of the foot. In particular, a heel region can be designed to be stiffer, and a region in the ball of the foot can be designed to be more flexible. This can be obtained through the size of the surface area of the individual layout layer. Different stiffnesses of this type can also be obtained through the surface area-dependent number of fibers of the fiber bundle. By way of example, one layout layer can extend over the entire surface area of the reinforcing structure, whereas in one region, a smaller number of tracks of the fiber bundle can be formed, and in another region, an increased number of tracks of fiber bundles can be formed, by means of which, in a similar manner, different stiffnesses or flexibilities can be configured. In addition, it is conceivable that in the edge region, in which a particular reinforcement should be provided, for example in the region in which the sole first makes contact with the floor when walking, a particularly large density of fiber bundles is implemented.

The reinforcing structure for the support body can advantageously exhibit a first layout layer, in which a laying out of the fiber bundle is only oriented in a unidirectional manner, such that, by this means, a base layout layer is formed. As a result, a basic strength and a fundamental transference of force can be obtained, in particular, the layout layer, preferably designed as an upper surface layer, can then provide a vectorial oriented strength. The continuous laid out fiber bundle can then be laid out oriented along lines of stress on a base layout layer of this type.

The reinforcing structure for the support body can furthermore comprise at least one layout layer, or base layout layer, respectively, in which the layout of the reinforcement of the fiber bundle is carried out in a crossing manner, and in particular the course of the filaments is oriented at a diagonal to the course of the lines of stress. As a result, a so-called torsional layout layer is formed. A torsional layout layer may be provided as a base layout layer, or as a second layout layer applied to a base layout layer, or inserted as an intermediate layer between, for example, two base layout layers. The continuous laid out fiber bundle can then be laid out on a layer of this type, oriented along lines of stress.

For the layout of the loading capacity of individual zones or regions of the support body, in particular in transition regions between support sections or between support sections and a connecting section, in which a transition from one large surface area to a tapered region or a diminished surface area also occurs, it is preferably provided that numerous layers of the fiber bundle are spaced closer or more tightly to one another, adjacent to one another, in part overlapping, and/or covering one another. By this means it is possible, at least in part, to set the bending capacity, torsional stiffness, and/or flexibility in individual regions in the reinforcing structure, and thereby in the support body. In addition, a cross-wise layout of the fiber bundle may also be provided, such that, for example, numerous adjacent or layered sections, running in a unidirectional manner, of the fiber bundle(s) are fixed to one another.

It is preferred that, between a first and one other support section, a tapered or reduced, in terms of surface area, connecting section, and a first layout layer having a unidirectional layout of the fiber bundle, are provided, in which, in the transition region between the support section and the tapered section, the fiber bundles are disposed such that they lie closely together, or even overlap in parts, or are layered on top of one another. This configuration enables a smooth transition at narrow sections, taperings or cross-section expansions, such as those, for example, in the transition region between two support sections or a support section and a connecting section. As a result, the stress concentration and crack formation resulting from loads can be significantly reduced.

Filament fibers, for example, made of carbon, glass, aramid, or similar materials, may be used as reinforcing fibers.

Preferably the orthosis is designed as an ankle-foot orthosis, in which the first support section is designed, at least in part, as a foot sole, which extends into at least one support section designed as a lower leg attachment, and a connecting section, designed as a brace between the foot sole and the lower leg attachment. With an ankle-foot orthosis of this type, the design of the support body with the reinforcing structure is particularly advantageous, because the brace can be designed to be thin, such that a greater wearing comfort and a very limited expansion of the shoe results. Moreover, the necessary dynamic load capacity can be adjusted and at the same time, a sufficient force transmission can be obtained. By means of the course of the fiber bundle oriented along lines of stress, moreover, a crack formation or stress concentration can be reduced in the transition region between the brace and the foot sole, in which a large change in the cross-section, and a change in the direction of stress, occurs, even with very limited radii adjusted to the anatomy of the human foot. With the design of the support body for use as an ankle-foot orthosis, it is preferably provided that the brace, running medially or laterally, transitions to the foot sole, and is disposed such that it runs in front of, over, or behind the ankle, running between the foot sole and the lower leg attachment. The use of the reinforcing structure, made of a support layer and having reinforcing fibers, enables a flexible design, having unchanging production conditions for the support body. As a result, with the same wearing comfort, an individual fitting of the orthosis to the patient can occur.

An objective of the invention, furthermore, is also attained by means of a method for the production of the orthosis. With this, it can be provided, in particular, that a reinforcing structure for a support body is produced, in which continuous laid out bundles of reinforcing fibers are applied to a support layer, in particular, sewn or stitched thereto, wherein the fiber bundles are laid out oriented along lines of stress, at least substantially corresponding to the stresses occurring in the support body, and the layout of the fiber bundles is carried out substantially within a surface area on the support layer, which corresponds to a two-dimensional layout of the support body. Subsequently the reinforcing structure, including the support layer and the fiber bundles sewn thereto is spatially molded and impregnated with a curable base material, such that a support body is formed.

Preferably it is provided that the bundles of the reinforcing fibers are applied to the support layer, and during, or immediately after the application, are sewn or stitched to the support layer. For this, a stitching or sewing machine may be used, applied to the continuous bundle during the stitching or sewing procedure.

The described production method enables not only an individual fitting of the shape of the support body to the physical contours of the patient, but also an individual adjustment regarding the dynamic load capacities, dependent on the physical geometry and the bodyweight of the patient. Thus, by means of this method, the production of an individualized orthosis is enabled in a simple manner. At the same time, with the layout of the fiber bundle, oriented along lines of stress, a more slender support body can be obtained, having the necessary stiffness and flexibility. Moreover, a method of this type enables a cost-effective production of the reinforcing structure, because fiber bundles are applied, or respectively, layout layers are formed, exclusively in the surface area of the support layer, which are subsequently needed for the formation of the support body. With prior methods, in which numerous textile layers are layered on top of one another to form a reinforcing structure, it is necessary that individual layers are cut from a length of material, or from individual sheets of this textile, resulting in significant waste. In particular with the use of carbon fiber textiles, a significant reduction in costs is obtained through this new method for the production of an orthosis. Furthermore, less trimming is needed, as a result of which, less carbon dust ends up in the environment. This results in a significant reduction of fire hazard in the production.

A preferred embodiment of the method provides that at least one layout layer is, in particular, sewn or stitched onto the support layer, and subsequently, the support layer is cut to the size of the surface area corresponding to the two-dimensional layout of the support body. In this manner, further processing is made easier. In particular, the post-production, after the lamination of the support layer with the fiber bundles, is significantly reduced. By means of the cutting of the support layers to size, the reinforcing structure is created from the two-dimensional layout of the support body that is to be produced, such that subsequently, only a post-production for rounding off edges or protrusions or suchlike is required, without the need for re-working the entire shape of the support body.

Furthermore, it is preferably provided that for each layout layer, a bundle of reinforcing fibers is sewn thereon in a continuous manner. In this manner, a simple and quick production, as well as an optimal flow of forces within a layout layer can be obtained. It is furthermore preferably provided that numerous layout layers are sewn and stitched onto the support layer. As a result, it is possible to enable that the bases following the fiber bundles are connected to one another with numerous layout layers, thus forming the support structure, and the support layer serves only as a coupling element between the individual fiber bundles until said fiber bundles have been laminated in a curable base material.

Figure 3A:
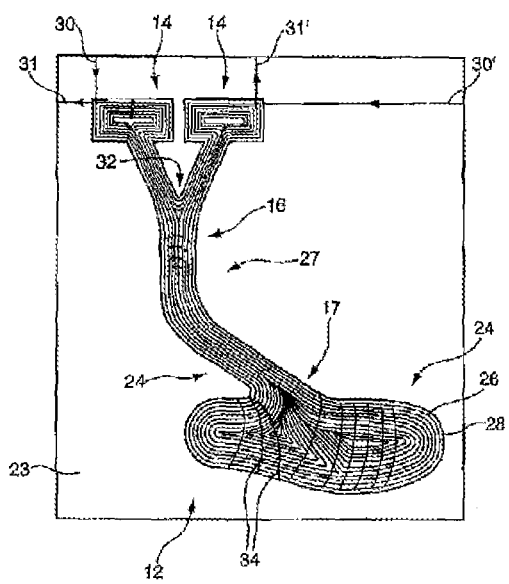
Figure 3B:
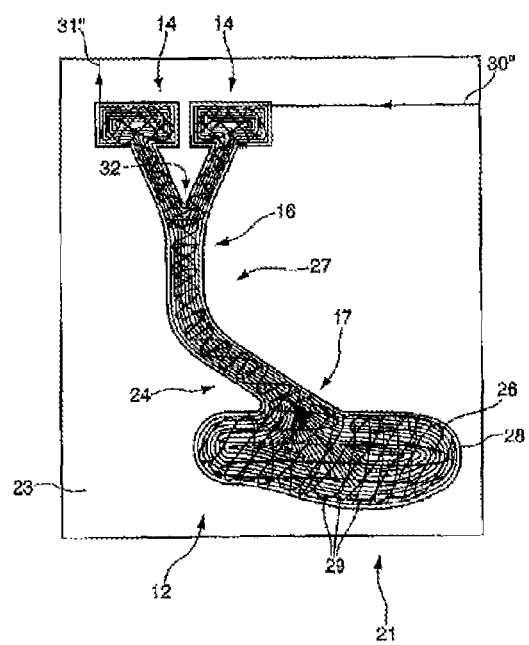
Figure 7A:
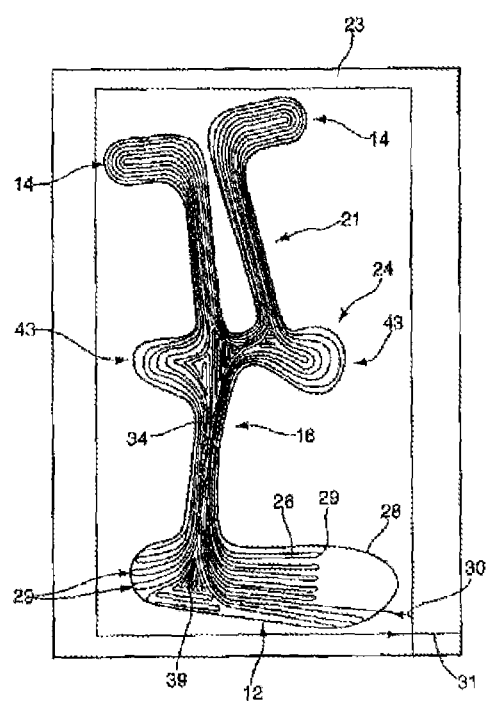
Figure 7B:
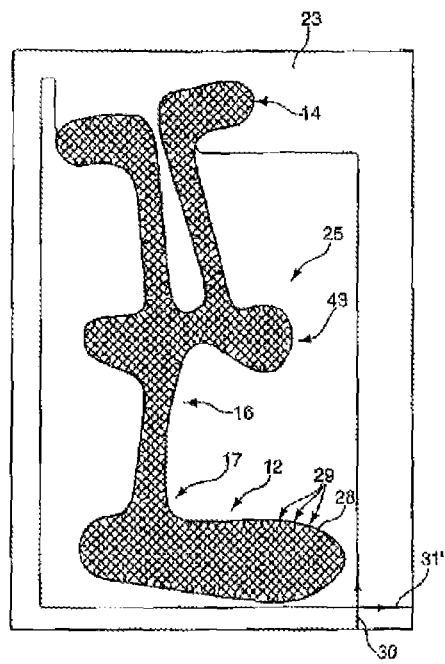
Figure 7C:
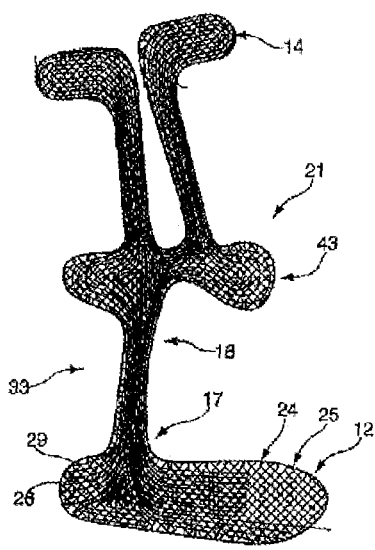
Figure 8:
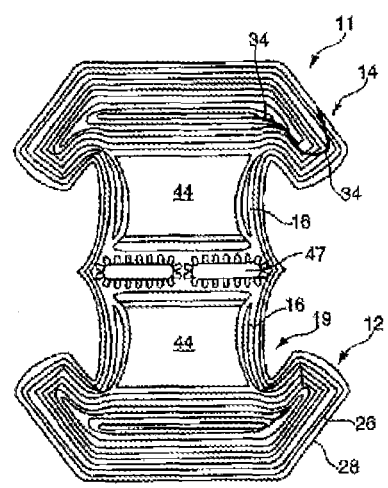
Figure 9:
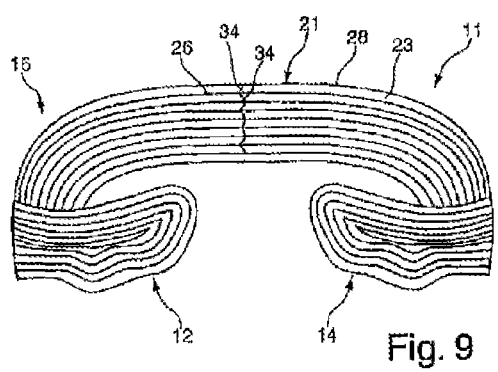

The invention, as well as other advantageous embodiments and developments thereof, shall be described and explained in greater detail below, based on the examples depicted in the drawings. The characteristics to be derived from the description and drawings may be used in and of themselves, or in numerous arbitrary combinations in accordance with the invention. They show:

FIG. 1 a perspective view of an orthosis according to the invention,

FIG. 2 a schematic side view of the orthosis according to FIG. 1,

FIGS. 3*a*-3*c* individual method steps for the production of the orthosis according to FIG. 1, FIG. 5 a schematic side view of the orthosis according to FIG. 1, FIG. 6 a schematic side view of the orthosis according to FIG. 5, FIGS. 7*a*-7*c* various schematic views for the production of a reinforcing structure for the orthosis according to FIG. 5, FIG. 8 a schematic front view of another alternative embodiment of the orthosis, and FIG. 9 a perspective view of a hip brace for a hip orthosis.

A first embodiment of an orthosis 11 is shown in perspective in FIG. 1. With this orthosis 11, an ankle-foot orthosis is concerned, by way of example, used with patients suffering foot drop or myasthenia in the lower extremities. This orthosis 11 comprises a first support section 12, designed, for example, as the foot sole. Furthermore, the orthosis 11 comprises at least a second support section 13, designed as a lower leg attachment. With this orthosis 11, the second support section 14 is provided as a calf attachment. A connecting section 16 is provided between the first and second support sections 12, 14, designed as a brace, bridging, as a single unit, the support section 12 and the support section 14. The support section 14 surrounds the calf, at least in part. In addition, there are fastening means, not shown, attached to the front free ends of the support section 14, such as Velcro bands or the like, for fastening the support section 14 to the lower leg. An ankle-foot orthosis of this type is also referred to as a lower leg orthosis.

A side view of the orthosis according to FIG. 1 can be seen in FIG. 2, comprising the support section 12, preferably approaching the anatomical shape of a foot sole. Furthermore, a transition region 17 is created between the first support section 12 and the connecting section 16, which tapers in the shape of a bridge starting from the foot sole, and is substantially directed, in relation to the horizontal orientation of the foot sole, vertically upward, and transitions into the connecting section 16, which extends in a first section behind the ankle toward the Achilles tendon and calf, and in a second section is guided upward along the calf, before said connecting section transitions into the upper support section 14.

This orthosis, depicted in FIGS. 1 and 2, is comprised of a support body 19, comprising the support sections 12 and 14 and the connecting section 16. This support body 19 includes a reinforcing structure 21, the structure of which is depicted in greater detail and described in FIGS. 3a-3c. The reinforcing structure 21 comprises a support layer 23, including a fiber reinforced non-woven or textile, in particular a polyamide non-woven or a carbon fiber or glass fiber reinforced non-woven or textile. This support layer 23 can be made available in the form of a belt or sheet. At least one layout layer 24 is applied to the support layer 23. This layout layer 24, in accordance with a first embodiment, is made of a continuous laid out bundle 26 of reinforcing fibers, which is sewn or stitched onto the support layer 23 by means of a thread. The course of the reinforcing fiber bundle, or, respectively, the layout of the fiber bundle 26 is determined by a surface area 27 on the support layer 23, corresponding to a layout of the three-dimensional support body 19 in a two-dimensional plane. Preferably the bundle 26 having reinforcing fibers, is laid out exclusively within said surface area 27. It is provided, preferably, thereby that for the formation of the continuous bundle 26, reinforcing fibers are laid out within the surface area 27 to form a layout layer 26. The bundle 26 may be formed, for this, in particular, of 24,000 individual, parallel carbon fibers.

It is preferred that first a continuous outer edge fiber bundle 28 is laid out, running along the edge of the surface area 27, and preferably entirely encircling said surface area 27. Subsequently to this, numerous unidirectional layers of the fiber bundle 26 may be applied, as is shown, for example, in FIG. 3a. In doing so, the orientation of the fiber bundle 26 is preferably configured along lines of stress corresponding to the stresses occurring in the orthosis 11. Likewise, it is also possible to first lay out the fiber bundle 26 within the surface area 27, and lay out the edge fiber bundle 28 afterwards. It is likewise possible that separate fiber bundles 26 be used for the layout of the edge fiber bundle 28 and the paths of the bundle disposed therein, respectively.

With this first layout layer 24, preferably the entire surface area 27 is first covered with a bundle of reinforcing fibers 26, wherein preferably a unidirectional orientation, meaning an orientation substantially in a single direction, back and forth, basically parallel to one another, or to the edge line, is selected. The fiber bundles 26 are laid out, for example, in the first support section 12, which forms the foot sole, with a greater spacing of the individual paths to one another, in order to first obtain a basic stability. In order that a sufficient stability is obtained in the transition region 17, the paths of the fiber bundles in this region lie close together, overlapping in part, or layered on top of one another. This has, on one hand, the advantage that continuous fiber bundles for the first layout layer can be worked with, by means of which a quick processing is enabled, without the occurrence of connecting knots. Furthermore, a transition having a favorable flow of forces is created, enabling an increased buckling load, ensuring a reduced crack formation. Alternatively, it can also be provided that individual sections or regions, both in the support sections 12 and 14, as well as in the connecting section 16, remain open or vacant. Likewise, individual regions can be formed with a significantly lower number of loops or paths of fiber bundles 26, by means of which the stiffness of the support sections 12 and/or 14 of the connecting section 16 is determined. In the example according to FIG. 3a, the laying out of the edge fiber bundle 28 occurs via a supply fiber bundle, or a supply bundle section 30 and the end of the fiber bundle 26 for the edge fiber bundle 28 is guided outward, and preferably cut off outside of the surface area 27 or the support layer 23. The layout layer 24 depicted in FIG. 3a forms a base layout layer, by means of which a certain surface stiffness of the orthosis 11 together with the support layer 23 is enabled. Furthermore, it may be provided with the embodiment according to FIG. 3 that for the paths of the fiber bundle 26 lying within the edge fiber bundle 28, a separate supply thread 30' and exit thread 31' are provided. Likewise, the fiber bundles 26 that form the edge fiber bundle 28 may be used. Any redirection of the fiber bundle 26 occurs preferably inside of the surface area 27, or, respectively, inside of the edge fiber bundle 28, or bordering on the edge fiber bundle 28, or overlapping said edge fiber bundle, but not, however, lying clearly outside of the edge fiber bundle 28. By means of this preferred design of the reinforcing structure 21, it is enabled through the application of the bundle 26 of reinforcing fibers, that transition regions having differing surface areas, such as, for example, between the foot sole and the brace, can be created, oriented along the flow of forces. This applies in an analogous manner to the transition regions between the connecting section 16 and the depicted support section 14.

According to a preferred embodiment, a forking 32 is not provided, and a support section 14, for example, is connected on the periphery of the two depicted support sections to a connecting section 16 having a continuous surface. Furthermore, a forking 32 of the connecting section 16, oriented along the flow of forces, can also be obtained by means of a layout technique of this type of the fiber bundle 26, such that both branches of the fork 32 are attached to the connecting section 16 in a manner optimized for loads.

The layout layer 24 is sewn or stitched to the support layer 23 such that at a later point in time, the support section 12 can be shaped in a larger angle range, for example between 70° and 110°, to the connecting section 16, to form a substantially horizontally oriented support section 12 for a foot sole, and a substantially vertically oriented connecting section 16 for a brace. This plasticity is only exemplary for this orthosis 11.

Depending on other implementations of orthoses, the shaping may also exhibit larger or smaller angles. Through the orientation of the paths of the fiber bundles 26, oriented along the flow of forces, a redirection of this type is favorable, and at the same time, the desired stiffness is maintained with a reduced wall thickness.

The fiber bundles 26 are sewn or stitched according to known techniques, wherein, for example, in the transition regions 17, comprising a cross-section change and/or spatially molded regions, in which a directional change in the plane of extension occurs, the individual sections of the fiber bundles 26 can be sewn with a certain amount of tolerance to the support surface 23, in order to accommodate said change, and to be able to adapt, at least to some degree, to said spatial modification. For the simple production of a layout layer 24 with a continuous fiber bundle 26, one or more redirected thread sections 34 may be provided, in order to create different pathways or structures of pathways, and thereby, if applicable, to also create different regions of strength.

To increase the stiffness of the reinforcing structure 21, a second layout layer 25 can be applied over the first layout layer 24. This is depicted, for example, in FIG. 3b, in that the second layout layer 25 is obtained through a cross-wise layout of the fiber bundle 26. The redirection regions 29 for the cross-wise layout of the fiber bundle 26 are provided, in particular, bordering on, on top of, or within, the edge fibers 28. By means of a cross-wise layout of this type, a torsional layer can be created. Instead of a torsional layer of this type, a cut-out textile layer may be used, corresponding to the shape of the support section, in particular a crossing pattern made of fiber bundles 26.

For the remaining structure of the reinforcing structure 21, additional layout layers may be applied, in particular in the transition region 17, which extend, for example, into the connecting section 16 and extend, at least in part, into the support section 12, in order to reinforce the transition region 17. Furthermore, different degrees of flexibility, or stiffness, respectively, of the foot sole may be set by means of the selection of the layout of the fiber bundle 26 in the support section 12, such that, for example, a heel region can be designed to be stiffer, and a region in the ball of the foot may be more supple, in order, in particular with foot drop, to act against a tightening of the foot, and at the same time, enabling a more pleasant loading of the foot, as a result of the more supple non-woven component.

After one or more layout layers 24, 25 in accordance with FIG. 3b have been sewn or stitched to the same support layer 23, the support layer 23 is cut out in relation to the surface area 27, such that an intermediate product 33, in accordance with FIG. 3c, is produced. Alternatively, it can furthermore be provided that another support layer is applied between individual layout layers, in order to sew another layout layer thereto, such that a multi-layer structure of support layers and layout layer is produced in place of the embodiment example depicted in FIG. 3b, in which a support layer and numerous layout layers are provided. As mentioned, a layout layer can also be formed from an accordingly cut out textile, in particular, a crossing layout pattern made of fiber bundles.

In a subsequent processing step an intermediate product 33 of this type is prepared for lamination, and pre-attached to a positive model 35. Subsequently, a casing 36 is imposed thereon, and a curable base material 38, for example, is poured therein via an opening 37. This curable base material concerns, for example, an acrylic or epoxy resin, or a thermoplastic resin, or similar material. This curable base material 38 is selected in accordance with the material of the support layer 23 and the fiber bundle 26. After pouring the base material 38 in the casing 36, and the complete impregnation, the intermediate product 33 is subjected to a vacuum. This results in a hardening of the base material 38. Subsequently, the casing 36 is removed from the positive mold 35, and the support body 19 formed thereby is removed from the positive model 35. Subsequently, the edges or edge region of the support body 19 are finished and connected, wherein with this finishing procedure it is preferred that damage to, or cutting through the edge fiber bundle 28 not occur. As a result, the closed course of the lines of stress can remain intact, by means of which an orthosis 11 is enabled, having a high degree of durability against wear and crack formation, and a high degree of wearing comfort.

An alternative embodiment of an orthosis 11 to that in FIGS. 1 and 2 is depicted in FIGS. 5 and 6. The fundamental design and function of this orthosis 11 corresponds to that of the first embodiment example. This orthosis 11 differs from the first embodiment, for example, in that the connecting section 16 in the lower region is disposed laterally, and not medially, to the first support section 12. Moreover, said connecting section 16 is disposed in front of the ankle 18. Alternatively, said connecting section can also run over or behind the ankle 18. In the embodiment example, two connecting sections 16 are depicted over the ankle, each supporting a support section 14. Alternatively, just one connecting section 16 can extend upward in front of the shin, and there receive a support section 14, which corresponds in size, for example, to the two depicted support sections 14. Likewise, the one connecting section 16 can exhibit a hole in the region of the shin, and comprise connecting sections 16 disposed to the sides of the shin, which lead to a support section 14. In particular, FIG. 6 shows that a bionic construction of the connecting section 17 in the region 40 is provided. Due to the design of the reinforcing structure 21, a tapering of this type of connecting section 17 in the ankle region is enabled, without resulting in an impairment to the dynamic load capacities of an orthosis 11 of this type. By way of example, this narrowed region 40 is enabled through a correspondingly narrow side-by-side layout of the fiber bundle 26, or, respectively, partial overlapping or layering having a sufficiently high degree of stiffness. Furthermore, through the production of the support body 19 from the reinforcing structure 21, an interlacing 42 in the connecting section 16 between the first and other support sections 12, 14 is also enabled, as can be derived from FIG. 5. As a result, an even better fitting of the connecting section 16 to the anatomic shape of the lower extremities is enabled, by means of which an increase in the thickness of the orthosis 11 can be further reduced. By means of the bionic construction of the connecting section 16 in the region 40 and/or the interlacing 42, both more space for the connecting section 16 within the opening of the shoe can be provided, and contact, increasing pressure between the ankle and the connecting section 16, can be prevented. At the same time there is no loss to the mechanical properties of the connecting section.

Furthermore, with an orthosis 11 of this type, an integration of alignment attachments 43, such as support elements, for example, can be incorporated, in a simple manner, in the support body 19. These lateral alignment attachments serve for improved alignment and positioning of the orthosis 11 on the body of the patient. Moreover, as a result of the production of the reinforcing structure 21 and its subsequent spatial plasticity for the production of the support body 19, it is also possible to enable that said alignment attachments 43 can be fitted and configured. As such, for example, a lower edge area of the alignment attachments may rest against the foot of the patient, not in a form-locking manner, but rather, it can be configured with a small amount of spacing thereto. This then has the advantage that during dynamic loading of the orthosis 11 in this region, no increase in pressure to the surface of the body via the orthosis 11 occurs, and nonetheless an anatomical form-locking application of the orthosis 11 is enabled. With this orthosis 11, in accordance with FIGS. 5 and 6, the connecting section 16 runs in front of and/or laterally to the shin. The production of the reinforcing structure 21 via the layout technique enables, optionally, a design of this type. This embodiment of the orthosis 11 includes, for example, a reinforcing structure 21 having a first layout layer 24 according to FIG. 7a. This layout layer 24 contains, for example, a continuous laid out bundle of reinforcing fibers 26, which extend to the ball of the foot, wherein the toe area is thereby, for the most part, excluded. Furthermore, it can be seen that in the transition region 17, the fiber bundles 26 run more closely together, and in part are overlapping as they transition to the connecting section 16. In a gusset 39 resulting therefrom, opposite the transition region 17, between the connecting section 16 and the support section 12, a gusset filling layout of the fiber bundle 26 is also introduced, in order to increase stiffness.

In FIG. 7b, another layout layer 25 is depicted as an example, comprising a cross-type layout pattern. The redirections 29 all lie on or within the edge fiber bundle 28, or, respectively, border thereon. For a better visualization, this layout layer 25 is depicted separately. With a construction of a support body 19 for the orthosis 11 according to FIGS. 5 and 6, the layout layer 24 is first applied to the support layer 23, for example, and subsequently the layout layer 25 is applied, according to 7b, or vice versa. In addition, another layout layer 24 or another embodiment of the layout layer can again be sewn or stitched over this, such that as a result, an intermediate product 33 in accordance with FIG. 7c is obtained. The remaining completion of the support body 19 from the intermediate product 33 according to FIG. 7c occurs in a manner analogous to the steps described in FIG. 3c.

Another alternative design of an orthosis 11 is depicted in FIG. 8. This orthosis 11 relates, for example, to a bridging frame for an MLO comfort orthosis. Connecting sections 16 are provided between a first and one other support section 12, 14, which are, however, spaced apart from one another by means of gaps 44. The connecting sections 16 comprise a central bridge 45, stiffening the connecting sections 16 with respect to one another. Additional, slot-shaped holes 47 are contained in the central bridge 45, which serve to accommodate fastening means, which are not shown in greater detail. The reinforcing structure 21 for the formation of the support body 19 is constructed in a manner analogous to that of the embodiments described above. In order to transfer the necessary support forces, the reinforcing structure 21 contains the layout layer 24, shown in an exemplary manner, having a continuous layout of the bundle 26 of reinforcing fibers. Other layout layers 24, 25 can also be provided, having different layouts of the fiber bundle(s) 26. It is preferred that the support layer 23 is disposed on the inner surface of the orthosis 11, and on the outer surface, at least the upper layout layer, and, if applicable, a layout layer lying under this, are visible. A configuration of this type can also apply for all other embodiment examples.

The embodiment examples described above show that the construction of a support body 19 from a reinforcing structure 21, including a support layer 23 and one or more layout layers 24, 25, having continuous laid out bundles 26 of reinforcing fibers, can be used for any orthoses 11, and through this shaping of the reinforcing structure 21, a specific fitting to the application surface on the body and to the dynamic loads, is provided. Furthermore, by means of a construction of an orthosis 11 of this type, a thickening in critical and heavily loadable regions can be reduced. As a result, the wearing comfort is increased. At the same time, by means of the formation of an edge fiber bundle 28, or the course of the fiber bundle 26 on the edge of the surface area 27 of the support layer 23, crack formation can be reduced.

Another alternative design of an orthosis 11 is shown, in part, in FIG. 9. This relates to a Dyna-Cox hip orthosis, by means of which orthotic treatment of a hip joint is facilitated. This orthosis 11 comprises a hip brace according to FIG. 9, as well as joints and bandages, not shown in greater detail, which engage with the thigh, in order to, acting together, secure the skeletal structure in order to prevent dislocations and to enable a support of the muscle development over the course of the entire care period. For this, a three-point principle is provided. The orthosis components provide, by means of the condyle attachment medial, the sub-trochanteric pad, and the resistance of the hip brace, a three-point principle of this type, and a dynamic securing of the joint head in the socket.

This hip brace comprises at least one first support section 12 and one other support section 14, connected to one another by at least one connecting section 16. By way of example, attachment means may be provided on the first and second support sections 12, 14, for fixing this hip brace to the hip.

The hip brace can, in part, be bound by bandages. The production of a hip brace of this type is carried out according to the principles of the previously described embodiments. The hip brace is depicted in FIG. 9, by way of example, with a layout layer 24, in particular as the uppermost layout layer, including a continuous laid out fiber bundle 26. Likewise, numerous layout layers 24, 25, as well as layout layers having other, alternative layout patterns of the fiber bundles 26, may be provided. First, a reinforcing structure 21, having a support layer 23 and one or more layout layers 24, 25, is produced, and designed as an intermediate product 33, in order to subsequently impregnate said reinforcing structure on the positive model 35 with the base material 38, and to further process said reinforcing structure, in order to obtain the finished shape depicted in FIG. 9. The embodiments and alternatives specified in the embodiment examples described above may also be provided in the production of this hip brace.

The invention claimed is:

1. A method for production of an orthosis having a first support section and at least one other support section forming a spatially shaped support body, the support sections being attachable to a patient, and configured to support limbs or upper body sections of a patient, the method comprising:
    applying, to a support layer, a continuous laid out fiber bundle formed from reinforcing fibers running parallel to one another, such that the fiber bundle is laid out, at least in part, corresponding to stresses occurring in the support body, oriented along lines of stress,
    the applied fiber bundle on the support layer forming a reinforcing structure for the support body,
    wherein the laying out of the fiber bundle is carried out within a surface area of the support layer, corresponding to a two-dimensional layout of the spatially shaped support body, and
    the support surface and the fiber bundle sewn thereto, are spatially shaped and impregnated with a curable base material.

2. The method according to claim 1, wherein the bundle of reinforcing fibers is applied to the support layer, and is sewn or stitched to the support layer.

3. The method according to claim 1, wherein after completion of the application of the fiber bundle to the support surface, which is cut to the shape of the surface area corresponding to the two-dimensional layout of the support body, the support surface is subsequently positioned on a positive model for lamination with the curable base material.

4. The method according to claim 1, wherein one or more layout layers are applied to the support layer.

\* \* \* \* \*